United States Patent [19]

Demole

[11] 4,197,862
[45] Apr. 15, 1980

[54] CYCLOALIPHATIC OXYGENATED DERIVATIVE AS FLAVORING INGREDIENT IN TOBACCO PRODUCTS

[75] Inventor: Edouard P. Demole, Coppet, Switzerland

[73] Assignee: Firmenich SA, Geneva, Switzerland

[21] Appl. No.: 800,846

[22] Filed: May 26, 1977

[30] Foreign Application Priority Data

May 31, 1976 [CH] Switzerland .......................... 6764/76

[51] Int. Cl.$^2$ ........................... A24B 3/12; A24D 1/18
[52] U.S. Cl. ..................................... 131/2; 131/17 R; 131/17 A; 131/144
[58] Field of Search ............. 131/2, 17 R, 15 R, 15 C, 131/144, 140 R, 140 C, 1 L; 426/538; 260/598

[56] References Cited

U.S. PATENT DOCUMENTS 3,940,499  2/1976  Pittet .................................. 131/17 R

OTHER PUBLICATIONS

*Perfume and Flavour Chemicals II* by Arctander, Published by Author in 1969 Montclair, N.J. (U.S.A.), Article 3001 Cited.

*Tobacco Flavoring for Smoking Products* by Leffingwell et al., Published by R. J. Reynolds Tobacco Company, 1972, pp. 59 and 63 Cited.

*Primary Examiner*—V. Millin
*Attorney, Agent, or Firm*—Pennie & Edmonds

[57] ABSTRACT

2, 6, 6-Trimethyl-3-oxo-cyclohex-1-en-carbaldehyde as a flavoring ingredient in tobacco products.

3 Claims, No Drawings

CYCLOALIPHATIC OXYGENATED DERIVATIVE AS FLAVORING INGREDIENT IN TOBACCO PRODUCTS

BACKGROUND OF THE INVENTION 2,6,6-Trimethyl-3-oxo-cyclohex-1-en-carbaldehyde, a compound of formula

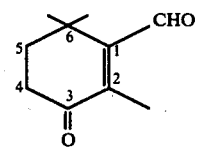

I has already been described in the scientific literature [see: Zh. Org. Khim. 4, 317 (1968), reported by Chem. Abstr. 68, 104589 u (1968)]; however, neither its organoleptic properties nor its utility in the flavour field have been mentioned therein.

We have now found that 2,6,6-trimethyl-3-oxo-cyclohex-1-en-carbaldehyde develops very useful gustative effects and consequently can be advantageously used in the flavour industry.

THE INVENTION

The present invention provides a process for the aromatization of foodstuffs, feedstuffs, beverages, pharmaceutical preparations and tobacco products which comprises adding thereto a small but flavouring effective amount of 2,6,6-trimethyl-3-oxo-cyclohex-1-en-carbaldehyde.

Further, this invention provides a tobacco, a tobacco substitute or a tobacco imitating product which comprises having added thereto as flavouring effective ingredient 2,6,6-trimethyl-3-oxo-cyclohex-1-en-carbaldehyde.

PREFERRED EMBODIMENTS OF THE INVENTION

The carbaldehyde of the invention can develop various gustative notes ranging from sweet, woody, more particularly pine-like, to green, hay- or straw-like notes. These flavouring characters confer great utility to the said carbaldehyde, namely for the aromatization of tobacco. However, 2,6,6-trimethyl-3-oxo-cyclohex-1-en-carbaldehyde, can also suitably be employed for the aromatization of various foodstuffs, beverages in particular, such as infusions or decoctions, tea, verbena, lime-blossom tea and camomile for example.

Interesting flavouring effects can be achieved with proportions ranging from about 1 to 100 ppm (parts per million) by weight of the compound of formula I, based on the weight of the product flavoured. When used as flavouring ingredient in a flavouring composition, the said compound can be used in proportions which obviously are much higher than the above given upper limit, for instance at concentrations of about 10 or 20%.

2,6,6-Trimethyl-3-oxo-cyclohex-1-en-carbaldehyde can be used in accordance with the invention on its own or, more frequently, in admixture with other flavouring ingredients, solvents or diluants. Suitable solvents include ethanol, diethyleneglycol and triacetine.

2,6,6-Trimethyl-3-oxo-cyclohex-1-en-carbaldehyde can be prepared according to a prior known process as illustrated hereinbelow:

Pathway 1:

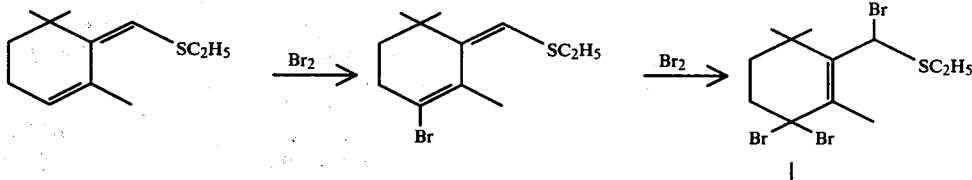

Pathway 2:

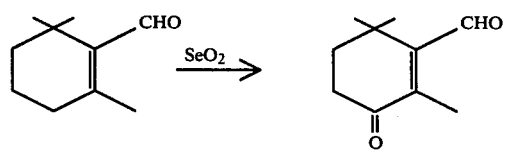

The invention relates further to a flavouring composition containing as effective ingredient 2,6,6-trimethyl-3-oxo-cyclohex-1-en-carbaldehyde.

Alternatively, 2,6,6-trimethyl-3-oxo-cyclohex-1-en-carbaldehyde can be synthesized by means of a novel process starting from α-cyclocitral. The said process is illustrated hereinbelow:

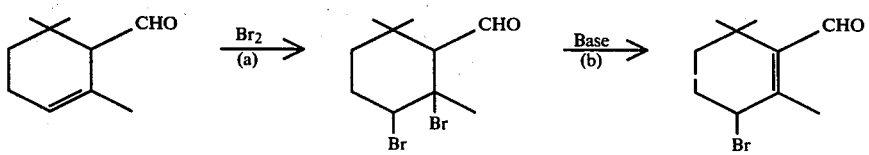

-continued

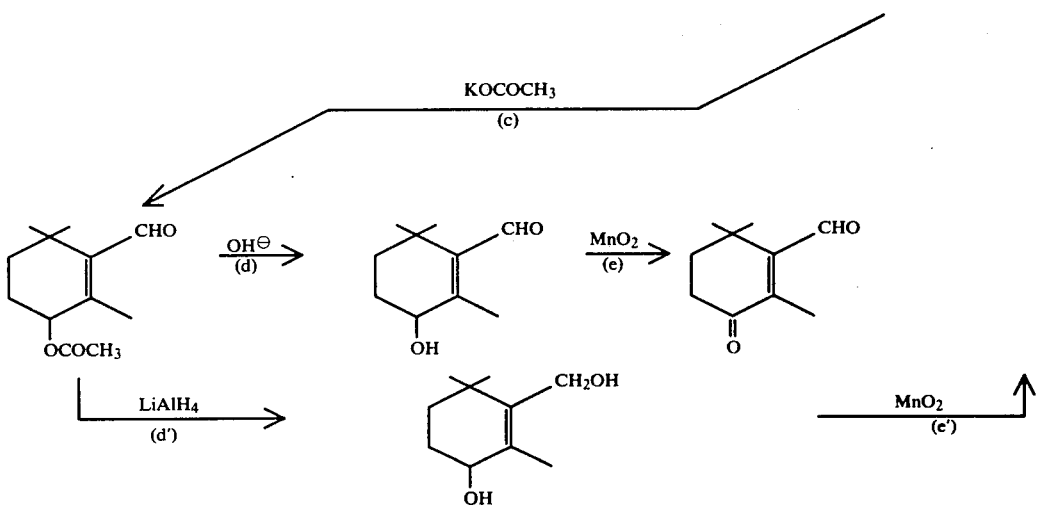

Reaction steps (a) and (b) can be effected in accordance with the procedure described in Tetrahedron Letters 1974, 3175.

(c): The bromide thus obtained (33 g) was kept under stirring at 20° C. for six days in the presence of 33 g of anhydrous potassium acetate in 300 ml of acetone. After filtration and evaporation of the clear filtrate, there were obtained 28 g of raw 2,6,6-trimethyl-3-acetoxy-cyclohex-1-en-carbaldehyde. A purification by column chromatography on 500 g of silicagel (eluant: toluene with increasing amounts of ethylacetate) yielded 10.0 g (yield=36% based on starting α-cyclocitral) of practically pure carbaldehyde.

(d): A solution of 5.0 g (23.8 mM) of the thus prepared carbaldehyde in 770 ml of acetonitrile and 480 ml (28.8 mM) of 0.06 N NaOH in water was stirred at 20° C. during 7 h in a nitrogen atmosphere. Work-up with ether, followed by separation of the organic phase, drying and evaporation, gave 3.4 g of raw product which by column chromatography on silicagel (100 g) (eluant: toluene with increasing amounts of ethylacetate), gave 2.38 g (yield=59%) of 2,6,6-trimethyl-3-hydroxy-cyclohex-1-en-carbaldehyde having b.p. 91°–93° C./0.001 Torr; $d_4^{20} = 1.0511$; $n_D^{20} = 1.5079$.

(e): A suspension of 1.9 g (11.3 mM) of the said hydroxy-carbaldehyde and 38 g of $MnO_2$, activated by heating it at 120° C. for 12 h, in 190 ml of methylene chloride were stirred at 20° C. for 3 days. After filtration, evaporation and subsequent distillation of the obtained residue, there were obtained 1.17 g (yield=62%) of 2,6,6-trimethyl-3-en-oxo-cyclohex-1-en-carbaldehyde having b.p. of about 90° C./0.001 Torr; $d_4^{20} = 1.0572$; $n_D^{20} = 1.5089$.

According to a variation of the above described method, 2,6,6-trimethyl-3-acetoxy-cyclohex-1-en-carbaldehyde can be reduced by means of $LiAlH_4$ according to step (d'), whereupon the thus obtained diol can be oxidized with $MnO_2$ to the desired oxo-aldehyde.

The invention is better illustrated by, but not limited to the following examples.

EXAMPLE 1

A black tea infusion was prepared by brewing 6 g of commercial black tea leaves in 1 liter of boiling water. After a few minutes brewing the infusion was put into clean cups in an amount of ca. 30 ml of solution per cup. To half of the cups there were added 0.6 ml of a 0.01% solution of 2,6,6-trimethyl-3-oxo-cyclohex-1-en-carbaldehyde in 95% ethanol (test solutions). These flavoured solutions were tasted by a panel of experienced flavourists who expressed their opinion by comparing them with the unflavoured beverages. This comparison showed that the test solutions possessed an additional natural straw-like gustative note of very pleasant character.

EXAMPLE 2

0.5 g of a 1% solution of 2,6,6-trimethyl-3-oxo-cyclohex-1-en-carbaldehyde in 95% ethanol were sprayed onto 100 g of a tobacco mixture of the "american blend" type. The tobacco thus flavoured was then used for the manufacture of "test" cigarettes the smoke of which was subjected to an organoleptic evaluation by a panel of flavour experts. These latter declared that the smoke of the test cigarettes presented a more marked straw-like character than that of the smoke of the "control" cigarettes the tobacco of which was simply treated with 95% ethanol.

What I claim is:
1. A process for the aromatization of tobacco products which comprises adding thereto a small but flavouring effective amount of 2,6,6-trimethyl-3-oxo-cyclohex-1-en-carbaldehyde.

2. A tobacco, a tobacco substitute or a tobacco imitating product which comprises having added thereto as flavouring effective ingredient 2,6,6-trimethyl-3-oxo-cyclohex-1-en-carbaldehyde.

3. The tobacco, tobacco substitute or tobacco imitating product according to claim 2, wherein 2,6,6-trimethyl-3-oxo-cyclohex-1-en-carbaldehyde is added in an amount of between about 1 and about 100 parts per million of the weight of the flavoured material.

* * * * *